United States Patent
Su et al.

(10) Patent No.: US 7,825,274 B2
(45) Date of Patent: Nov. 2, 2010

(54) BISBIPHENYLACYLPHOSPHINE OXIDE AND PREPARATION METHOD THEREFORE

(75) Inventors: Wen-Chiung Su, Longtan Township, Taoyuan County (TW); Chang-Chih Lin, Longtan Township, Taoyuan County (TW); Ching-Shang Sheng, Longtan Township, Taoyuan County (TW)

(73) Assignee: Chung Shan Institute of Science and Technology, Taoyuan County (TW)

( * ) Notice: Subject to any disclaimer, the term of this patent is extended or adjusted under 35 U.S.C. 154(b) by 230 days.

(21) Appl. No.: 12/141,380

(22) Filed: Jun. 18, 2008

(65) Prior Publication Data

US 2008/0287701 A1 Nov. 20, 2008

Related U.S. Application Data

(62) Division of application No. 11/337,441, filed on Jan. 24, 2006, now Pat. No. 7,465,819.

(51) Int. Cl.
*C07F 9/02* (2006.01)
(52) U.S. Cl. ....................................... 558/82
(58) Field of Classification Search .................... 558/82
See application file for complete search history.

(56) References Cited

U.S. PATENT DOCUMENTS

| | | | |
|---|---|---|---|
| 4,292,152 | A | 9/1981 | Lechtken et al. |
| 4,710,523 | A | 12/1987 | Lechtken et al. |
| 4,737,593 | A | 4/1988 | Ellrich et al. |
| 4,868,091 | A | 9/1989 | Boettcher et al. |
| 5,008,426 | A | 4/1991 | Kleiner et al. |
| 5,407,969 | A | 4/1995 | Kleiner et al. |

FOREIGN PATENT DOCUMENTS

EA EU 0413657 7/1990

WO WO-00/64956 11/2000

*Primary Examiner*—Rei-tsang Shiao
(74) *Attorney, Agent, or Firm*—Rabin & Berdo, P.C.

(57) ABSTRACT

A bisbiphenylacylphosphine oxide of formula (I) and its preparation method are provided. The formula of —Ar— is

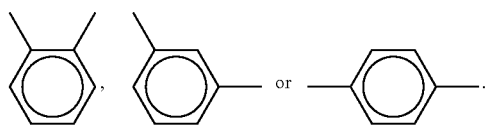

First, 10-chloro-9,10-dihydro-9-oxa-10-phosphaphenanthrene (CDOP) is prepared by using 2-phenylphenol, and then is esterified to synthesize 6-methoxy-(6H)-dibenz[c,e][1,2]oxa-phosphorin (MDOP). Next, acid chloride compounds are added for performing the Arbuzov reaction to synthesize bisbiphenylacylphosphine oxide. CDOP is hydrolyzed to be derived into 9,10-dihydro-9-oxa-10-phosphaphen-anthrene-10-oxide (DOPO), and then DOPO reacts with arylaldehyde to form secondary alcohol. Therefore, bisbiphenylacylphosphine oxide is prepared by using secondary alcohol under oxidation. Also, under a coupling reaction, DOPO reacts with the acid chloride compounds by using a Lewis acid as a catalyst to prepare bisbiphenylacylphosphine oxide.

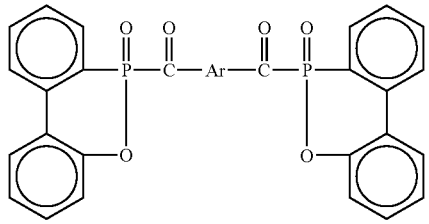

11 Claims, No Drawings

BISBIPHENYLACYLPHOSPHINE OXIDE AND PREPARATION METHOD THEREFORE

CROSS-REFERENCE TO RELATED APPLICATION

This application is a divisional of copending application Ser. No. 11/337,441, filed Jan. 24, 2006, the entire disclosure of which is incorporated herein by reference.

BACKGROUND

1. Field of Invention

The invention relates to a photoinitiator and a preparation method thereof and in particular to a bisbiphenylacylphosphine oxide and its preparation method.

2. Related Art

A photoinitiator is a spectacular compound that can absorb a specific wavelength of photo energy to release free radicals by a cleavage or β cleavage. Therefore it can be used as an initiator for a monomer chain reaction. Most photoinitiators have the properties of low price, good stability, no toxicity, no colorizing, easy to make, long life span free radical and good light absorption rate. Recently, the demand for its application has driven the development of low energy and long wavelength light initiators, with most of the initiators consisting of a carbonyl chromophoric group. In a light wavelength range of 300 nm to 400 nm and based on the Norrish Type I, a photoinitiator of biphenylacryphosphine oxide can directly release free radicals without the assist of a sensitizer, so that it can be directly used for polymerizing acrylics.

Most of the acryphosphine oxides such as those disclosed in U.S. Pat. Nos. 5,407,969, 5,008,426 and European patent 413657 belong to an aliphatic group, a phenyl group or a monophenylacryphosphine oxide and have remarkable effects in practice. However, the light initiator compound should have greater equivalent to make the polymerization more efficient. Thus, how to develop a high equivalent compound for a light initiator has become an important topic in the field.

SUMMARY

One object of the invention is to provide a bisbiphenylacylphosphine oxide and a preparation method therefore.

According to the invention, a bisbiphenylacylphosphine oxide can be represented by the following structural formula (I):

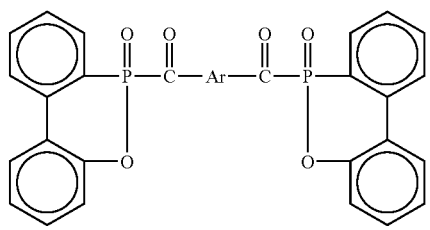

wherein —Ar— is a phenyl group, and the phenyl group can be

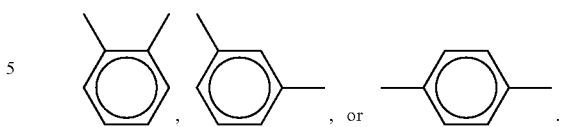

According to the invention, an embodiment of a method for preparing a bisbiphenylacylphosphine oxide is provided where the bisbiphenylacylphosphine oxide has the structural formula (I) and —Ar— is a phenyl group. The method includes the steps of: heating an excess phosphorus trichloride and a 2-phenylphenol with a catalyst to form a 10-chloro-9,10-dihydro-9-oxa-10-phosphaphenanthrene (CDOP) where the CDOP is represented by the following structural formula (II); removing the remaining phosphorus trichloride; esterifying the CDOP to become a 6-methoxy-(6H)-dibenz[c,e][1,2]oxa-phosphorin (MDOP) where the MDOP is represented by the following structural formula (III); and conducting an Arbuzov reaction with the MDOP and a acid chloride compound to form the bisbiphenylacylphosphine oxide, which has the following structural formula (I).

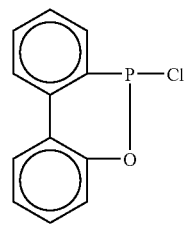

(II)

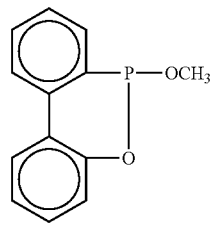

(III)

According to the invention, another embodiment of a method for preparing a bisbiphenylacylphosphine oxide is provided where the bisbiphenylacylphosphine oxide has the structural formula (I) and —Ar— is a phenyl group. The method includes the steps of: heating an excess phosphorus trichloride and a 2-phenylphenol with a catalyst to form a 10-chloro-9,10-dihydro-9-oxa-10-phosphaphenanthrene (CDOP) where the CDOP is represented by the following structural formula (II); removing the remaining phosphorus trichloride; hydrolyzing the CDOP to form a 9,10-dihydro-9-oxa-10-phosphaphen-anthrene-10-oxide (DOPO) where the DOPO is represented by the following structural formula (IV); conducting an addition and oxidization reaction or a coupling reaction with the DOPO to form the bisbiphenylacylphosphine oxide, which has the structural formula (I).

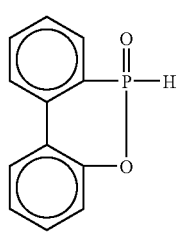

(IV)

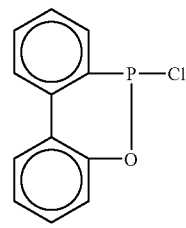

The DOPO can conduct an addition reaction with an arylaldehyde to form a secondary alcohol, followed by mixing the secondary alcohol with an oxidant to form the bisbiphenylacylphosphine oxide, which has the structural formula (I).

Or, the DOPO can conduct a coupling reaction with an acid chloride compound and a catalyst to form the bisbiphenylacylphosphine oxide, which has the structural formula (I).

DETAILED DESCRIPTION

First, add an excess phosphorus trichloride ($PCl_3$), a 2-phenylphenol and a tiny amount of catalyst such as zinc chloride ($ZnCl_2$) into a reactor; then conduct a first step of an esterifying reaction by heating at temperature of 30 to 80° C. and under normal pressure for one hour; next, raise the temperature to 150 to 200° C. for 6 hours to conduct the second step of an thermo-dynamic trans-esterification and intramolecular cyclization; use a $^{31}P$ nuclear magnetic resonance ($^{31}PNMR$) to measure the end point of the reaction; and after the reaction is completed, recycle the remaining phosphorus trichloride; then an intermediate 10-chloro-9,10-dihydro-9-oxa-10-phosphaphenanthrene (hereinafter refer to as CDOP) is obtained. This reaction is shown equation (1), (1)

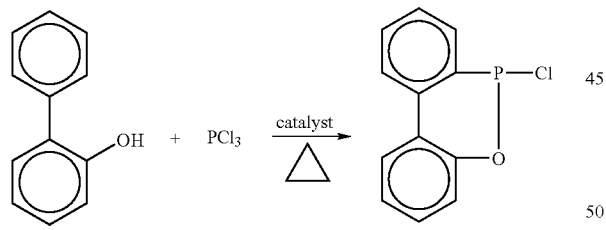

where

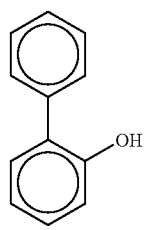

is the structural formula of the 2-phenylphenol, and is the structural formula of the CDOP.

Next, add a methanol ($CH_3OH$) and a triethylamine (($C_2H_5$)$_3$N) to the CDOP in toluene ($C_7H_8$) to conduct an esterifying reaction; then distill the solution to produce a 6-methoxy-(6H)-dibenz[c,e][1,2]oxa-phosphorin (hereinafter referred to as MDOP); and mix the MDOP and an acid chloride compound to conduct an Arbuzov reaction at a temperature of 60 to 140° C. for synthesizing the bisbiphenylacylphosphine oxide. This reaction is shown equation (2), (2)

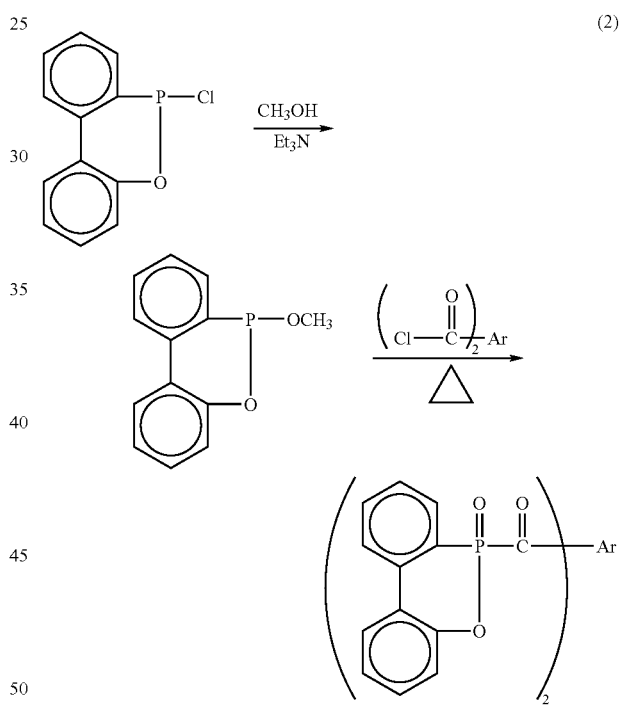

where

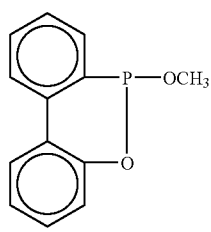

is the structural formula of the MDOP,

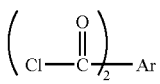

is the structural formula of the acid chloride compound, and

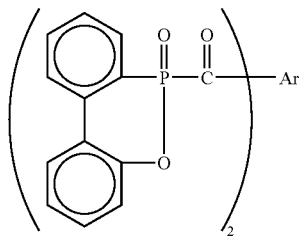

is the structural formula of the bisbiphenylacylphosphine oxide. In these structural formulas, —Ar— is the phenyl group, which can be a

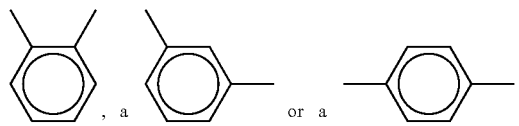

When —Ar— is

the bisbiphenylacylphosphine oxide will be 1,2-bis(6-(6H)-dibenz[c,e][1,2]oxaphosphorin-6-oxide) benzoate (hereinafter referred to as PCPO); when —Ar— is

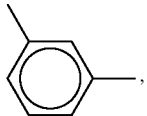

the bisbiphenylacylphosphine oxide will be 1,3-bis(6-(6H)-dibenz[c,e][1,2]oxaphosphorin-6-oxide) benzoate (hereinafter referred to as ICPO); and when —Ar— is

the bisbiphenylacylphosphine oxide will be 1,4-bis(6-(6H)-dibenz[c,e][1,2]oxaphosphorin-6-oxide) benzoate (hereinafter referred to as TCPO).

Additionally, the CDOP can be hydrolyzed to 9,10-dihydro-9-oxa-10-phosphaphenanthrene-10-oxide (hereinafter referred to as DOPO), followed by conducting an addition reaction with an arylaldehyde for obtaining a secondary alcohol; next this secondary alcohol is oxidized to a bisbiphenylacylphosphine oxide. The reaction is shown equation (3),

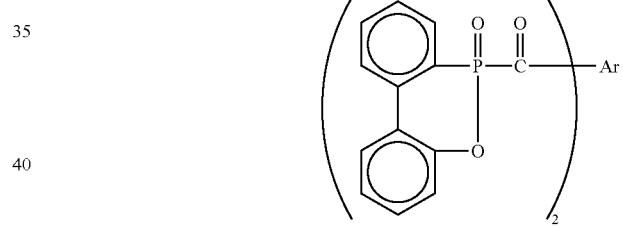

(3)

where

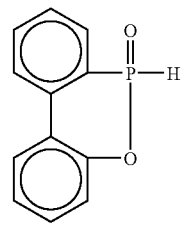

is the structural formula of the DOPO,

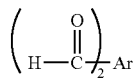

is the structural formula of the arylaldehyde, and

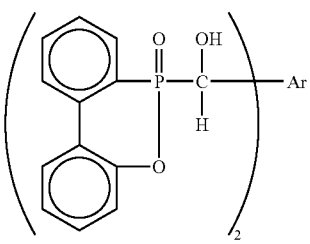

is the structural formula of the secondary alcohol. When —Ar— is

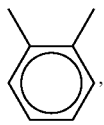

the secondary alcohol is 1,2-bis(6-(6H)-dibenz[c,e][1,2]oxaphosphorin-6-oxide)benzyl alcohol (hereinafter referred to as PHCPO); when —Ar— is

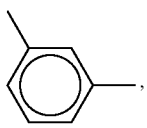

the secondary alcohol is 1,3-bis(6-(6H)-dibenz[c,e][1,2]oxaphosphorin-6-oxide)benzyl alcohol (hereinafter referred to as IHCPO); and when —Ar— is

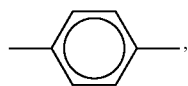

the secondary alcohol is 1,4-bis(6-(6H)-dibenz[c,e][1,2]oxaphosphorin-6-oxide)benzyl alcohol (hereinafter referred to as THCPO).

Also, a Lewis acid can be used as a catalyst for the DOPO and the acid chloride compound to conduct a coupling reaction to produce a bisbiphenylacylphosphine oxide, which is shown equation (4).

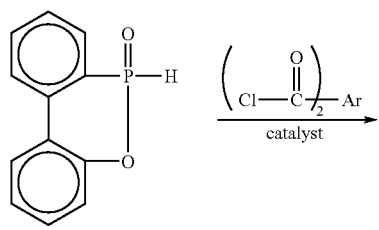

(4)

-continued

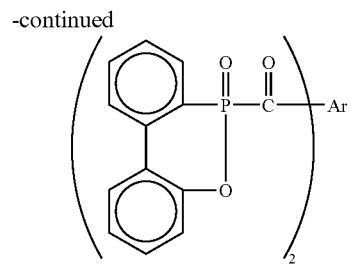

EMBODIMENT 1

1. Synthesis of CDOP

Add one mole of 2-phenylphenol (about 170 g), 1.1 moles of phosphorus trichloride (about 151 g) and 0.01 moles of zinc chloride (about 1.36 g) into a reactor. Then install a dropping bottle between the reactor and the condenser; the dropping bottle has a pressure balance tube and a controlling valve. The condenser is maintained at about 0° C. and is connected to a ventilated tube at the top. Then, the ventilated tube communicates to a neutralization sink by a dry tube. Raise the solution to about 30° C. for initiate the reacting. The temperature will maintain at 60° C. to 80° C. during the reaction. After an hour of reaction, the hydrochloric acid vapor producing rate by the reaction between the phosphorus trichloride and the 2-phenylphenol will slow down.

In the second step of thermo-dynamic trans-esterification and intramolecular cyclization. Here, the temperature is raised and the phosphorus trichloride is continually distilled out and then condensed in the dropping bottle. When the temperature is raised to about 110° C., start to slowly drop back the phosphorus trichloride from the dropping bottle. Then, continually raise the temperature to about 180° C. After 6 hours, when the hydrochloric acid vapor is barely being produced, the reaction can probably be finished. Here, sample the solution to proceed with the $^{31}$PNMR test to accurately determine the reaction end point. The CDOP can be obtained by decompressed distilling the remained solution, and the phosphorus trichloride can be recycled during the decompressed distilling process.

Next, introduce 500 milliliter toluene into the reactor where the CDOP is. After stirring and still for a moment; a sticky polyphosphate precipitates and adheres to the wall of the reactor. After filtering the mixture and distilling out the toluene, a 233 g of CDOP can be obtained. The yield is approximately 100%.

2. Synthesis of MDOP

After the phosphonating reaction, add one mole of CDOP with 500 milliliter toluene into the reactor. Then drop a mixture solution with about one mole of methanol and one mole of triethylamine into the reactor. Stir the solution while raising the temperature to 50° C. After continuously dropping the mixture solution into the reactor for an hour, keep stirring it for another hour. Next, the produced triethylamine hydrichloride $((C_2H_5)_3N·HCl)$ is precipitated by giving the reactor an ice bath. After filtering the precipitated triethylamine hydrochloride, recycle the toluene solvent by distillation. Then, the MDOP can be obtained by distillation under a condition of decompressing (about 1 mmHg) and at a temperature of 140 to 150° C. The yield is about 92%.

3. Synthesis of PCPO

Add 0.2 moles of MDOP (about 46 g) and 0.1 moles of phthaloyl chloride (about 20.3 g) into the reactor and heat them for 2 hours under a temperature of 120° C. When the reaction is completed, decompress it (about 20 mmHg to 30 mmHg) for 5 minutes. After that, white solid powders can be obtained. After returning the products to the room temperature, use toluene to rinse out the un-reacted reactants. Then, the toluene contained products are further filtered and dried to get the PCPO. The yield is about 45%.

4. Synthesis of ICPO

Add 0.2 moles of MDOP (about 46 g) and 0.1 moles of isophthaloyl chloride (about 20.3 g) into the reactor and heat them for 2 hours under a temperature of 120° C. When the reaction is completed, decompress it (about 20 mmHg to 30 mmHg) for 5 minutes. After that, white solid powders can be obtained. After returning the products to room temperature, use toluene to rinse out the un-reacted reactants. Then, the toluene contained products are further filtered and dried to get the ICPO. The yield is about 63%.

5. Synthesis of TCPO

Add 0.2 moles of MDOP (about 46 g) and 0.1 moles of terephthaloyl chloride (about 20.3 g) into the reactor and heat them for 2 hours under a temperature of 120° C. When the reaction is completed, decompress it (about 20 mmHg to 30 mmHg) for 5 minutes. After that, white solid powders can be obtained. After returning the products to room temperature, use toluene to rinse out the un-reacted reactants. Then, the toluene contained products are further filtered and dried to get the TCPO. The yield is about 85%.

EMBODIMENT 2

1. Synthesis of DOPO

Add one mole of CDOP with a 500 milliliter toluene into a reactor. Add one mole of water (about 18 g) by dropping for about one hour. The condenser uses water for cooling. The hydrochloric acid vapor is lead to the neutralization sink by going through the ventilated tube which connects to the top of the condenser. When the dropping is finished, reflux it for an hour. Then introduce the nitrogen into the solution, reflux it for another 2 hours for blowing out the remaining hydrochloric acid vapor. After return to room temperature, white solid DOPO precipitates. The yield is about 95% after filtering and dying.

2. Synthesis of PHCPO, IHCPO and THCPO

Dissolve 0.1 moles of DOPO (about 21.6 g) with 0.05 moles of 1,2-phthalaldehyde or 1,3-phthalaldehyde, or 1,4-phthalaldehyde (each about 6.7 g) respectively in an about 50 milliliter toluene for reflux 6 hours. After returning the solution to room temperature, white solid powders precipitate. The toluene can be further used to rinse out the un-reacted reactants. Next, they are filtered and dried and then a 28% yield PHCPO, a 41% IHCPO and an 85% THCPO can be respectively obtained.

3. Oxidation Reaction for PHCPO, IHCPO and THCPO

Dissolve 0.005 moles of PHCPO or IHCPO or THCPO (each about 2.83 g) in a 20 milliliter dimethyl sulfoxide (DMSO) respectively, and use 0.8 g manganese dioxide ($MnO_2$) to be the oxidant for reacting 24 hours at about 70° C. Then after returning the solution to room temperature and quench by water, white solid powders precipitates.

About 1.3 g of oxalyl chloride (($ClCO)_2$) can be used as the oxidant for reacting 24 hours at room temperature. When water is used to end the reaction, white solid powders precipitates.

In the oxidization step with manganese dioxide, the PHCPO has a PCPO yield of 68%, the IHCPO has an ICPO yield of 71%, and the THCPO has a TCPO yield of 82% after drying. On the other hand, in the oxidization step with the oxalyl chloride, the PHCPO has a PCPO yield of 47%, the IHCPO has an ICPO yield of 61%, and the THCPO has a TCPO yield of 72% after drying.

EMBODIMENT 3

Add 0.2 moles of DOPO (about 43.2 g) with 0.1 moles of phthaloyl chloride or isophthaloyl chloride or terephthaloyl chloride (each about 20.3 g) respectively into a reactor. Then add 0.3 g aluminium trichloride as a catalyst and about 50 milliliter toluene into the reactor with reflux 4 hours. After the reaction completes and the solution is returned to room temperature, white solid powders precipitate. The toluene can be further used to rinse out the un-reacted reactants after filtering. After they are dried, a 25% yield PCPO, a 45% ICPO and a 76% TCPO can be respectively obtained.

Identify the synthesized compounds and intermediates with the infrared spectroscopy (IR). The main peaks located around 900 $cm^{-1}$-1050 $cm^{-1}$, 1645 $cm^{-1}$, and 1230 $cm^{-1}$ are identified as P—O bond, C=O bond, and P=O bond, respectively. The O—H bond spectrums of IHCPO, PHCPO, and THCPO locate around 3230 $cm^{-1}$. By using the $^1H$ NMR to identify the synthesized compounds and intermediates, the chemical shift of a methoxy group of the MDOP is 3.5 ppm and exhibits two peaks because of the coupling effect of the phosphorous, this coupling constant is about 10 Hz. The chemical shift of the P—H bond of the DOPO is around 8.0 ppm, and it has a coupling constant of about 600 Hz. Except for the absorption of the hydrogen groups on the benzene ring of the PHCPO, IHCPO and THCPO, the chemical shift of the hydrogen on the benzyl group is between 5.1 ppm and 5.5 ppm. The chemical shifts of the hydrogen groups on the benzene ring of the PCPO, ICPO and TCPO are between 7.4 ppm and 8.4 ppm. Furthermore, by using a mass spectrometry (MS) to identify the synthesized compounds and intermediates, the molecular weight for PCPO, ICPO and TCPO are determined as 562. And the base peak is P—C bond cleavage, identifies 347 and 215 fragment ion peak. The molecular weight of the PHCPO, IHCPO and THCPO are 566 and the base peak of the C—P bond cleavage, identifies fragment ion peak 351. In addition, phosphine oxide has its own specific absorption positions. Therefore a $^{31}PNMR$ can be used to identify the structure of the compound. Please refer to the following table 1, showing the structural formula of compounds and the relative signal absorption positions.

TABLE 1

| Compound | Structural formulas | Relative signal absorption position |
|---|---|---|
| CDOP | (dibenzofuran-phosphorus-Cl structure) | 134.1 ppm |
| MDOP | (dibenzofuran-P-OCH$_3$ structure) | 129.2 ppm |
| PCPO | (bis-phosphinate structure, ortho-phenylene diketone bridge) | 21.8 ppm |
| ICPO | (bis-phosphinate structure, meta-phenylene diketone bridge) | 22.1 ppm |
| TCPO | (bis-phosphinate structure, para-phenylene diketone bridge) | 22.3 ppm |
| DOPO | (dibenzofuran-P(=O)-H structure) | 15.4 ppm |

TABLE 1-continued

| Compound | Structural formulas | Relative signal absorption position |
|---|---|---|
| PHCPO | | 31.2 ppm |
| IHCPO | | 31.4 ppm |
| THCPO | | 31.6 ppm |

What is claimed is:

1. A preparation method for bisbiphenylacylphosphine oxide, the bisbiphenylacylphosphine oxide represented by the following structural formula (I),

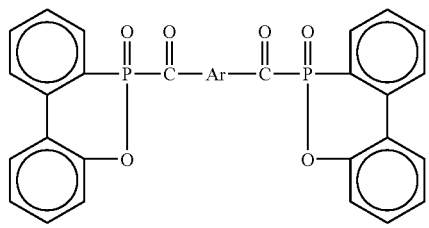
(I)

wherein —Ar— is a phenyl group, the method comprising:
heating an excess phosphorus trichloride and a 2-phenylphenol with at least one catalyst to form a 10-chloro-9,10-dihydro-9-oxa-10-phosphaphenanthrene (CDOP) wherein the CDOP is represented by the following structural formula (II);

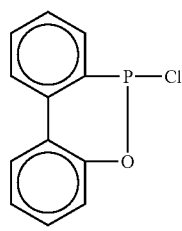
(II)

removing the remaining phosphorus trichloride;

hydrolyzing the CDOP to form a 9,10-dihydro-9-oxa-10-phosphaphen-anthrene-10-oxide (DOPO) wherein the DOPO is represented by the following structural formula (IV); and

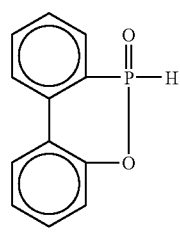
(IV)

conducting one of an addition and oxidization reaction and a coupling reaction with the DOPO to form the bisbiphenylacylphosphine oxide which has the structural formula (I).

2. The preparation method of claim 1 wherein the step of conducting one of an addition and oxidization reaction and a coupling reaction with the DOPO includes:
conducting an addition reaction with the DOPO and at least one arylaldehyde to form a secondary alcohol; and
mixing the secondary alcohol with at least one oxidant to form the bisbiphenylacylphosphine oxide which has the structural formula (I).

3. The preparation method of claim 2 wherein the step of oxidization reaction proceeds in an organic solvent.

4. The preparation method of claim 3 wherein the organic solvent is dimethyl sulfoxide.

5. The preparation method of claim 2 wherein the oxidant is selected from the group consisting of an oxalyl chloride and a manganese dioxide.

6. The preparation method of claim 1 wherein the step of conducting one of an addition and oxidization reaction and a coupling reaction with the DOPO includes:

conducting the coupling reaction with the DOPO, at least one acid chloride compound and at least one catalyst to form the bisbiphenylacylphosphine oxide which has the structural formula (I).

7. The preparation method of claim 6 wherein the catalyst is a Lewis acid.

8. The preparation method of claim 7 wherein the Lewis acid is aluminium trichloride.

9. The preparation method of claim 1 wherein the catalyst is zinc chloride.

10. The preparation method of claim 1 wherein a mole ratio of the phosphorus trichloride to the 2-phenylphenol in the step of heating an excess phosphorus trichloride and a 2-phenylphenol is between 1.1 and 1.2.

11. The preparation method of claim 1 wherein the step of heating an excess phosphorus trichloride and a 2-phenylphenol proceeds under a temperature range of 30° C. to 200° C.

* * * * *